United States Patent

Dumler et al.

[11] Patent Number: 5,699,578
[45] Date of Patent: Dec. 23, 1997

[54] CLEANING DEVICE

[75] Inventors: Norbert Dumler; Bernd Fellner, both of Ansbach, Germany

[73] Assignee: georg karl geka-brush GmbH, Bechhofen-Waizendorf, Germany

[21] Appl. No.: 605,017

[22] PCT Filed: Aug. 13, 1994

[86] PCT No.: PCT/EP94/02713

§ 371 Date: Feb. 28, 1996

§ 102(e) Date: Feb. 28, 1996

[87] PCT Pub. No.: WO95/06444

PCT Pub. Date: Mar. 9, 1995

[30] Foreign Application Priority Data

Aug. 31, 1993 [DE] Germany ............ 9313034 U

[51] Int. Cl.$^6$ ............ A61C 15/00; A46B 3/18
[52] U.S. Cl. ............ 15/167.1; 15/22.1; 15/206; 15/207.2; 132/321; 132/322; 132/329
[58] Field of Search ............ 15/141.1, 167.1, 15/167.3, 206, 207.2, 22.1; 132/218, 320, 321, 322, 329; 401/129; 433/3, 216

[56] References Cited

U.S. PATENT DOCUMENTS

| | | | |
|---|---|---|---|
| 60,013 | 11/1866 | King | 15/206 X |
| 458,090 | 8/1891 | Zimmermann | 15/141.1 |
| 2,627,621 | 2/1953 | Bardugon | 15/206 |
| 2,690,569 | 10/1954 | Kozerski | 15/206 X |
| 3,878,580 | 4/1975 | Stöhr et al. | 15/206 X |
| 4,053,959 | 10/1977 | Wiley | 15/167.1 X |
| 5,123,841 | 6/1992 | Millner | 433/125 |
| 5,230,356 | 7/1993 | Villas | 132/329 |
| 5,253,386 | 10/1993 | LaLonde | 15/206 |

FOREIGN PATENT DOCUMENTS

| | | |
|---|---|---|
| 91 11 499.3 | 3/1993 | Germany . |
| 6503 | of 1885 | United Kingdom ............ 15/206 |
| 1230503 | 5/1971 | United Kingdom ............ 15/207.2 |
| 1572804 | 8/1980 | United Kingdom ............ 15/207.2 |
| 86/02532 | 5/1986 | WIPO . |

*Primary Examiner*—Mark Spisich
*Attorney, Agent, or Firm*—Browdy and Neimark

[57] ABSTRACT

In a cleaning device, in particular for the interdental area, comprising two twisted, wire-type sections (1, 2), it is provided, with a view to putting into practice novel cleaning methods, the cleaning being accompanied by the application of care and cleaning agents, that the wire-type sections (1, 2) are twisted in such a way that at least one free loop or eye (9) is formed.

5 Claims, 2 Drawing Sheets

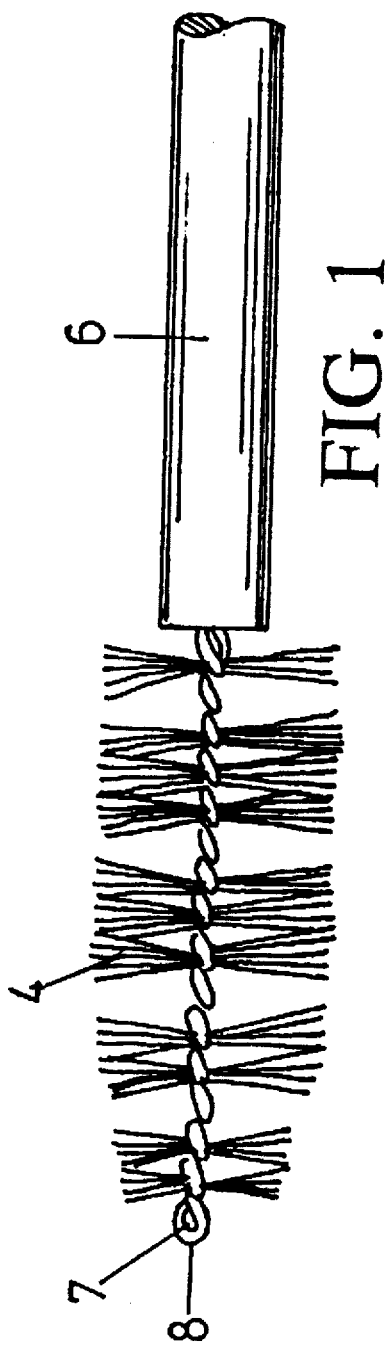
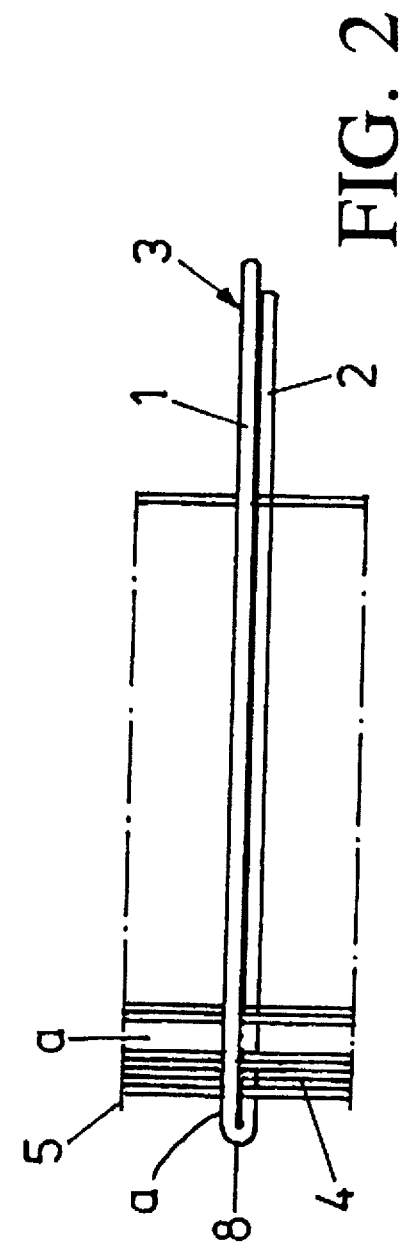

5,699,578

CLEANING DEVICE

BACKGROUND OF THE INVENTION

1. Technical Field of the Invention

The invention relates to a cleaning device, in particular for the interdental area, comprising two twisted, wire-type sections.

2. Prior Art

Cleaning devices of the generic type are known per se as interdental brushes, i.e. with bristles inserted in between the twisted wire sections. The known cleaning devices of the generic type substantially make use of the cleaning effect of the inserted bristles, the twisted wire segments only serving to retain the bristles.

In addition, cleaning devices for the interdental area are known, which are of toothpick-type shape, i.e. they consist of a tapering thorn-type part of wood, plastic material or metal, it also being known to roughen the surface of such plastic parts by flocking or to provide them with fibers.

OBJECT AND SUMMARY OF THE INVENTION

It is the object of the invention to embody a cleaning device of the generic type such that it becomes possible to provide novel cleaning methods, the cleaning being accompanied by the application of care and cleaning agents.

According to the invention, this object is solved in that the wire-type sections are twisted in such a way that at least one free loop or eye is formed.

An eye or loop extended from the oblong basic configuration may serve as the actual cleaning and care device on the one hand, on the other hand it can retain a fluid or paste when it is dipped into such agent, owing to the surface tension of such an agent. When the fluid or paste is taken from a reservoir, it can then be dispensed by contact with the tooth or gums.

In particular, provision can be made for the wire-type sections to be formed by bows bent in the shape of a U, an eye or loop being formed in the vicinity of the bight of the U. Consequently, this eye or loop is formed at the front end of the device, its exposed position making it especially suitable for dental treatment.

It can in particular be provided that the loop or eye at the extreme end is triangular or rhomboidal.

By advantage, the wire-type sections may consist of at least one plastic fiber, i.e. it is not necessary for them really to be of wire or of plastic-coated wire in the manner known per se, because plastic fibers—combined with corresponding fillers, if required—are available that exhibit a wire-type behavior, i.e. they remain in their position after the twisting, not showing any tendency towards restoring.

In keeping with another embodiment of the invention, it can be provided that the wire-type sections form a loop over a substantial part of their length, twisting only being provided at one end portion. In the vicinity of the twisted end, such a configuration favorably comprises a handle or holder member, respectively, to be inserted into a rotating or oscillating appliance. For instance, this is the way in which to provide a cleaning device combined with an electric drive as known from electric toothbrushes.

Furthermore, in order to provide for a brush-type configuration, a cleaning device according to the invention can be embodied in such a way that radially extending fibers or bunches of fibers are inserted in between the twisted wire-type sections. Consequently, such a device can also be used as a conventional brush, in particular an interdental brush.

The fibers extending radially may contain abrasive additives such as silicon carbide or aluminum oxide increasing the cleaning effect.

DETAILED DESCRIPTION OF THE DRAWINGS

Details of the invention will become apparent from the ensuing description of preferred embodiments, taken in conjunction with the drawing, in which FIG. 1 shows a brush-type configuration, with the cleaning device according to the invention;

FIG. 2 shows the embodiment according to FIG. 1 prior to the twisting of the wire sections, FIG. 3 shows an exemplary embodiment of designing the tip portion according to FIG. 1, FIG. 4 shows an exemplary embodiment of forming loops in the central portion of the tip according to FIG. 1, and FIG. 5 shows an exemplary embodiment in the form of an insert for an electric-motor-driven appliance.

DETAILED DESCRIPTION OF THE PREFERRED EMBODIMENT(S) OF THE INVENTION

In the embodiment according to FIGS. 1 and 2, two wire-type sections 1, 2 consisting of a plastic fiber 3 are bent in the shape of a U. Bristles 4 are inserted in between the wire-type sections 1, 2, forming an envelope curve 5, so that they stick out radially as bunches or bristles after the twisting of the sections, as seen in FIG. 1. The free ends may be provided with a handle member 6.

Portions a that do not have any bristles are provided between the individual bristles 4. The twisting of the sections 1, 2 is such that a loop 7 will form at the free extreme end 8 corresponding to the bight of the U and wherever there are no bristles, i.e. at the portions a without bristles.

When embodied in this way, a brush, for instance an interdental brush, can be employed in such a manner that the loop 7 at the free end is used for the treatment of teeth and interdental gaps, a cleaning agent being collected when the brush in dipped into it and being applied in the dental area.

Figure 3:
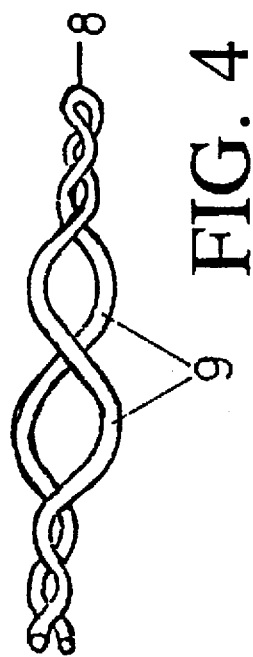
FIG. 3 illustrates a preferred, substantially rhomboidal embodiment of the loop 7a at the free end 8.
Figure 4:
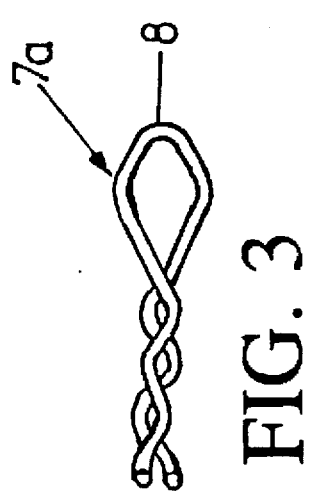
FIG. 4 shows loops or eyes 9 formed in the central portion of the sections 1, 2.
Figure 5:
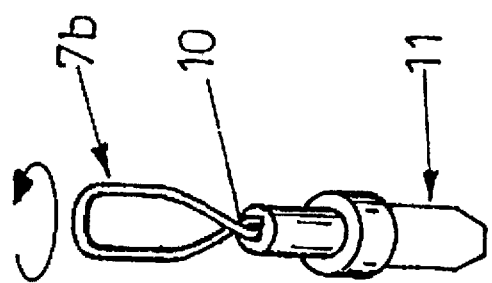

In the embodiment according to FIG. 5, provision is made for a single great loop 7b, the wire-type sections 1, 2 being twisted only in the vicinity of the inner end 10, where they are inserted into the holder 11—only diagrammatically outlined—which can be inserted into an electric-motor-driven appliance.

We claim:

1. A cleaning device for use in an interdental area, said cleaning device having a holding member and radially extending fibers inserted in between two twisted wire-type sections (1, 2) to form a brush, a first end of said two twisted wire-type sections being engaged in said holding member, said cleaning device comprising at least one open loop or eye formed at a free second end of the two twisted wire-type sections, said two twisted wire-type sections consisting of at least one plastic fiber and being formed from a bow bent in the shape of a U, the open loop or eye being formed in a vicinity of a bight of the U, said radially extending fibers containing an abrasive additive selected from the group consisting of silicon carbides and aluminum oxide.

2. The cleaning device according to claim 1, wherein the loop or eye is triangular.

3. The cleaning device according to claim 1, wherein the loop or eye is rhomboidal.

4. The cleaning device according to claim 1, wherein the holding member can be inserted into an oscillating appliance.

5. A cleaning device for use in the interdental area, said cleaning device having a holding member, said cleaning device comprising two wire sections formed from a plastic fiber bow bent in the shape of a U, an elongated open loop being formed in a vicinity of a bight of the U at the free first end of said two wire sections, an insertion portion formed by twisting a second end of said two wire sections together, said elongated loop extending to said insertion portion, a holding member, said insertion portion engaged in said holding member up to said elongated loop, wherein said holding member can be inserted into an oscillating appliance for use in cleaning the interdental area.

\* \* \* \* \*